(12) United States Patent
Alfaro et al.

(10) Patent No.: US 10,940,248 B2
(45) Date of Patent: Mar. 9, 2021

(54) SYSTEMS AND METHODS FOR RECOVERING WHITE BLOOD CELLS FROM A LEUKOREDUCTION FILTER

(71) Applicant: Fenwal, Inc., Lake Zurich, IL (US)

(72) Inventors: Jo Anne B. Alfaro, Arlington Heights, IL (US); Yoshikazu Mizobuchi, Mundelein, IL (US)

(73) Assignee: FENWAL, INC., Lake Zurich, IL (US)

( * ) Notice: Subject to any disclaimer, the term of this patent is extended or adjusted under 35 U.S.C. 154(b) by 553 days.

(21) Appl. No.: 15/829,789

(22) Filed: Dec. 1, 2017

(65) Prior Publication Data
US 2018/0169311 A1    Jun. 21, 2018

Related U.S. Application Data

(60) Provisional application No. 62/436,169, filed on Dec. 19, 2016.

(51) Int. Cl.
| | | |
|---|---|---|
| *A61K 31/7004* | (2006.01) | |
| *A61M 1/02* | (2006.01) | |
| *A61M 1/34* | (2006.01) | |
| *A61M 1/36* | (2006.01) | |
| *B01D 21/26* | (2006.01) | |
| *B01D 63/16* | (2006.01) | |

(52) U.S. Cl.
CPC ....... *A61M 1/0218* (2014.02); *A61K 31/7004* (2013.01); *A61M 1/025* (2013.01);
(Continued)

(58) Field of Classification Search
CPC .. F01M 11/03; B01D 35/005; B01D 46/2414; B01D 36/006; B01D 29/88; B01D 29/21; B01D 35/153; B01D 35/16; B01D 2201/295; B01D 29/94; B01D 24/38; B01D 24/44; B01D 2201/291; B01D 33/0006; B01D 33/06; B01D 61/24; B01D 61/243; B01D 19/0052; B01D 21/26; B01D 63/16; A61M 1/38; A61M 1/0213; A61M 1/3627; A61M 1/02; A61M 1/0218; A61M 1/3644; A61M 1/3633; A61M 1/265;
(Continued)

(56) References Cited

U.S. PATENT DOCUMENTS

| | | |
|---|---|---|
| 5,868,696 A | 2/1999 | Giesler et al. |
| 6,268,119 B1 | 7/2001 | Sumita et al. |

(Continued)

FOREIGN PATENT DOCUMENTS

| | | |
|---|---|---|
| EP | 1683857 A1 | 7/2006 |
| EP | 2671600 A1 | 12/2013 |

(Continued)

OTHER PUBLICATIONS

Partial European Search Report for application No. 17207890.9, dated May 9, 2018, 13 pages.

(Continued)

*Primary Examiner* — Angel Olivera
(74) *Attorney, Agent, or Firm* — Cook Alex Ltd.

(57) ABSTRACT

A method of recovering white blood cells from a leukoreduction filter, the method comprising providing a solution comprising a sugar, flowing a volume of the solution through a leukoreduction filter containing captured white blood cells, and collecting elute from the leukoreduction filter, wherein the elute comprises the solution and recovered white blood cells.

14 Claims, 4 Drawing Sheets

(52) U.S. Cl.
CPC ........ *A61M 1/3496* (2013.01); *A61M 1/3636* (2014.02); *B01D 21/26* (2013.01); *B01D 63/16* (2013.01); *A61M 2202/0439* (2013.01)

(58) Field of Classification Search
CPC .............. A61M 1/3496; A61M 1/0209; A61M 1/3643; A61M 2202/0439; A61M 1/3683; A61M 1/3686; A61M 1/3692; A61M 1/3693; A61M 1/3696; A61M 1/3636; A61M 1/025; A61K 31/7004
See application file for complete search history.

(56) References Cited

U.S. PATENT DOCUMENTS

| | | | |
|---|---|---|---|
| 6,544,751 B1 * | 1/2003 | Brandwein | C12N 5/0634 435/7.1 |
| 9,782,707 B2 | 10/2017 | Lynn et al. | |
| 9,796,166 B2 | 10/2017 | Verri et al. | |
| 2015/0265755 A1 | 9/2015 | Lynn et al. | |

FOREIGN PATENT DOCUMENTS

| | | |
|---|---|---|
| EP | 2987511 A1 | 2/2016 |
| WO | 2014039086 A1 | 3/2014 |

OTHER PUBLICATIONS

Extended European Search Report for application No. 17207890.9, dated Sep. 5, 2018, 11 pages.

\* cited by examiner

SYSTEMS AND METHODS FOR RECOVERING WHITE BLOOD CELLS FROM A LEUKOREDUCTION FILTER

CROSS-REFERENCE TO RELATED APPLICATIONS

This application claims the benefit of U.S. Provisional Patent App. No. 62/436,169 filed Dec. 19, 2016, which is expressly incorporated herein by reference in its entirety.

FIELD OF THE DISCLOSURE

The present disclosure relates generally to blood separation systems and methods and, in particular to blood separation systems and methods also involving recovering white blood cells from a leukoreduction filter.

BACKGROUND

The separation of blood into its components is commonly performed in apheresis procedures, in which blood components are separated while a donor or patient is connected to a separation system (sometimes referred to as a "chairside" procedure), or with previously-collected whole blood, in whole blood manufacturing or component processing procedures. For example, a common procedure is the separation of whole blood into plasma and red blood cells (RBCs).

Such separation procedures may be highly automated, utilizing a single-use fluid circuit comprising containers of various solutions, such as saline, anticoagulant and additive solution (commonly containing a saline, adenine, and glucose medium), as well as cassettes comprising defined fluid pathways, as well as containers for the receipt of the separated blood components, all of which are interconnected by fluid flow paths in the form of tubing to a separation device, such as a centrifuge or a spinning membrane separator. The fluid circuit is associated with a durable hardware component which has pumps and clamps associated therewith that operatively engage the tubings to circulate the blood and its separated components through the associated single-use fluid circuit. The durable hardware component may include a programmable controller to automatically operate the pumps, clamps and separator in accordance with the desired apheresis procedure.

Before transfusing collected blood components to a recipient in need of a component, or before subjecting blood components to treatment, it may be desirable to minimize the presence of materials that may cause undesired side effects in the recipient. For example, because of possible reactions, it may be desirable to reduce the number of leukocytes in blood components before storage and/or before transfusion (i.e., "leukoreduction"). Such leukoreduction may be accomplished by flowing the blood components through a leukoreduction filter (also called a leukofilter) that captures white blood cells (WBCs) by requiring passage of the component through a filter medium that retains leukocytes and other components/aggregates while allowing the remaining components to pass through the medium and be collected for subsequent transfusion and/or storage.

SUMMARY

According to an exemplary embodiment, the present disclosure is directed to a method of recovering white blood cells from a leukoreduction filter. The method comprises providing a solution comprising a sugar, flowing a volume of the solution through a leukoreduction filter containing captured white blood cells, and collecting elute from the leukoreduction filter, wherein the elute comprises the solution and recovered white blood cells.

According to an exemplary embodiment, the present disclosure is directed to a method for automated recovery of white blood cells from a leukoreduction filter. The method comprises providing a durable separation hardware controlled by a programmable controller driven by software, said hardware configured to associate with a disposable sterile circuit comprising a separator and a leukoreduction filter. The hardware and disposable sterile circuit are configured by the programmable controller to separate a white blood cell-containing fluid into a primary fluid constituent and a secondary fluid constituent, collect the secondary fluid constituent in a first container, direct in a first flow direction the primary fluid constituent through a leukoreduction filter configured to capture white blood cells and other retentate while not capturing filtrate, collect the filtrate flowing out of the leukoreduction filter in a second container, direct in a second flow direction a volume of solution comprising a sugar through the leukoreduction filter, and collect in a third container a first volume of elute flowing out of the leukoreduction filter, wherein the first volume of elute comprises the solution and recovered white blood cells.

According to an exemplary embodiment, the present disclosure is directed to a solution for recovering white blood cells from a filter, the solution comprising phosphate buffered saline and a sugar comprising L-rhamnose.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

DETAILED DESCRIPTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

Some embodiments may increase the concentration of white blood cells removed from a leukofilter.

Some embodiments may improve and facilitate the removal of white blood cells from leukofilters.

It may be desirable to harvest white blood cells captured by leukofilters after the leukofilters have been used. White blood cells, such as T-lymphocytes and B-lymphocytes may be used in cellular therapies and certain cancer therapies. Leukofilters that have previously captured leukocytes may be sources of functional white blood cells.

Figure 1:
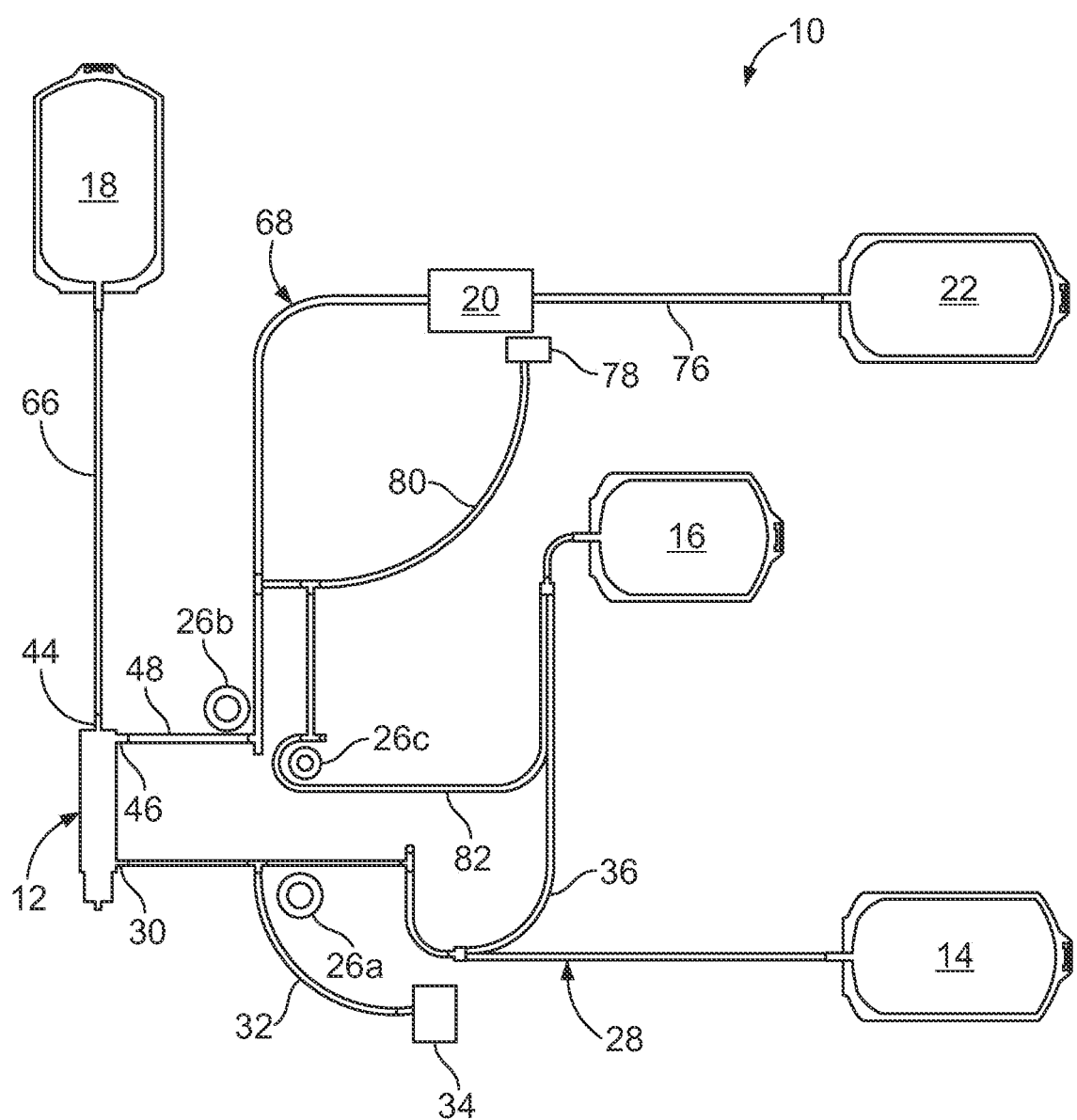
FIG. 1 is a front elevational view of a disposable fluid flow circuit for use in combination with a durable, reusable separation system, according to an exemplary embodiment.

FIG. 1 illustrates a disposable fluid flow circuit 10 having a separator 12 for use in combination with a durable, reusable separation system which controls flow through the fluid flow circuit 10 to separate blood components, e.g., red blood cells, from blood, e.g., anticoagulated whole blood. In one embodiment, the separator 12 may be a spinning membrane separator. One example of a spinning membrane separator, disposable fluid flow circuit, and durable separation system is described in PCT Patent Application Publication No. WO 2014/039086 A1 which is herein incorporated by reference in its entirety, although any suitable separator, disposable circuit, and separation system may be used. In another embodiment, the separator may be a centrifugal separator. One example of a centrifuge separator is described in U.S. Pat. No. 5,868,696, which is herein incorporated by reference in its entirety, although any suitable separator may be used.

The disposable fluid flow circuit 10 as illustrated in FIG. 1 includes various components interconnected by flow paths, which may be variously configured. In one embodiment, one or more of the flow paths between the components of the circuit 10 may be defined by flexible plastic tubing, but the flow paths may be otherwise configured without departing from the scope of the present disclosure. The disposable circuit 10 may include a fluid source container 14, an additive container 16, a separator 12, a secondary fluid constituent collection container 18, a leukocyte reduction filter 20, and a red blood cell collection container 22. The fluid flow circuit 10 may be pre-assembled and pre-sterilized, although certain components (e.g., fluid source container 14 and/or additive container 16) may be separately provided and sterilely connected to the circuit 10. The various containers may be hung from hangers or hooks of the separation system, and/or one or more of the containers may be associated with the separation system, e.g., by placing a container on a horizontal surface, such as a weigh scale). Pumps may be provided to control flow through the circuit 10. For example, certain portions of the flow path may be engaged by fluid pumps 26a-26c (e.g., peristaltic pumps) of the separation system, which may cause the passage of fluid through the circuit 10.

The fluid source container 14 may be any suitable container, such as a flexible plastic pouch or bag in which a white blood cell-containing fluid (e.g., approximately 450 ml of whole blood) has been previously collected. The container 14 may be separate from the fluid circuit 10 during collection from a fluid source, allowing the white blood cell-containing fluid to be more easily collected and stored before being joined to the rest of the fluid circuit 10, or may be connected with the circuit 10 at the time of collection. The container 14 may be provided with an amount of anticoagulant prior to (or following) the introduction of the white blood cell-containing fluid into the container 14 and before the anticoagulated fluid is flowed out of the container 14 to prevent premature coagulation.

An inlet flow path 28 may be attached to the fluid source container 14, such as by a sterile connection device or other suitable attachment mechanism, and may define a fluid flow path from the container 14 to an inlet 30 of the separator 12. The inlet flow path 28 may include additional components (e.g., fluid control valves or clamps) and junctions and branches, such as a flow path branch 32 that may be associated with a pressure sensor 34 of the separation system and/or a flow path branch 36 that may be associated with the additive container 16.

A portion of the inlet flow path 28 may be configured to be acted upon by an inlet pump 26a of the separation system for actively pumping fluid through the inlet flow path 28 and into the separator 12. In one embodiment, the inlet pump 26a may be provided as a peristaltic pump that operates by progressive compression or squeezing of a portion of the inlet flow path 28.

A secondary fluid constituent (characterized by having a smaller diameter, lower density, and/or lower mass for separation purposes), such as plasma, separated by the separator 12 may flow from an outlet port 44, through a secondary fluid constituent flow path 66, and into a storage container 18, which may be of any suitable material compatible with storage of the secondary fluid constituent. Similarly, from the separator 12, a primary fluid constituent (characterized by having a larger diameter, higher density, and/or higher mass for separation purposes), such as red blood cells and/or white blood cells may flow through another outlet port 46 and through a primary fluid constituent flow path 48, which may form part of an outlet flow path 68. The separated red/white blood cells may be pumped through the outlet flow path 68 under action of a red/white blood cell or outlet pump 26b of the blood separation system. The outlet pump 26b may be configured and operate substantially the same way as the inlet pump 26a or it may be differently configured (e.g., as a flexible diaphragm pump). In an embodiment in which the separator 12 is a membrane separator, the secondary fluid constituent flow path 66 may lack an associated pump, as the volumetric flow rate therethrough may be effected by the difference between the volumetric flow rate of the inlet pump 26a and the volumetric flow rate of the outlet pump 26b.

In one embodiment, the white blood cell-containing fluid pumped into the separator 12 may be whole blood, and the separator 12 may function to separate the blood into concentrated red/white blood cells and virtually cell free plasma. Packed red/white blood cells at approximately 80-85% hematocrit may be pumped out of the separator 12 through the primary fluid constituent flow path 48. In another embodiment, the white blood cell-containing fluid may be different from whole blood, and the nature of the separated red/white blood cells (e.g., hematocrit) and the nature of the other fluid constituent from which the red/white blood cells are separated may vary.

Figure 2:
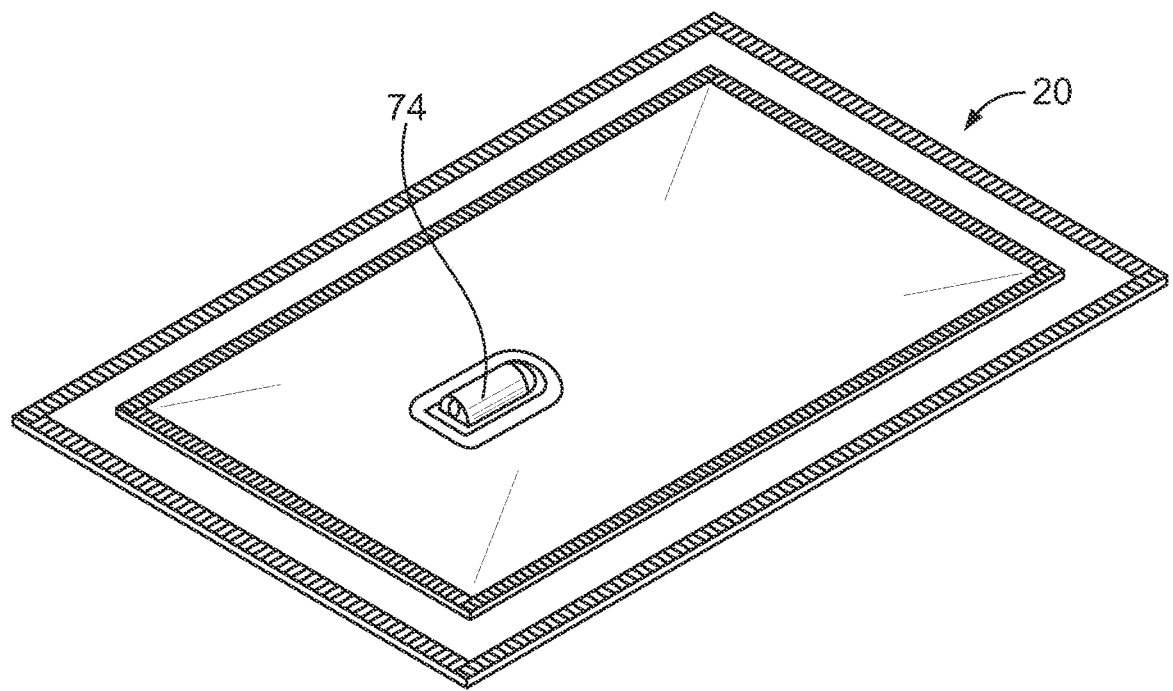
FIG. 2 is a front perspective view of a leukoreduction filter of the fluid flow circuit of FIG. 1, according to an exemplary embodiment.
Figure 3:
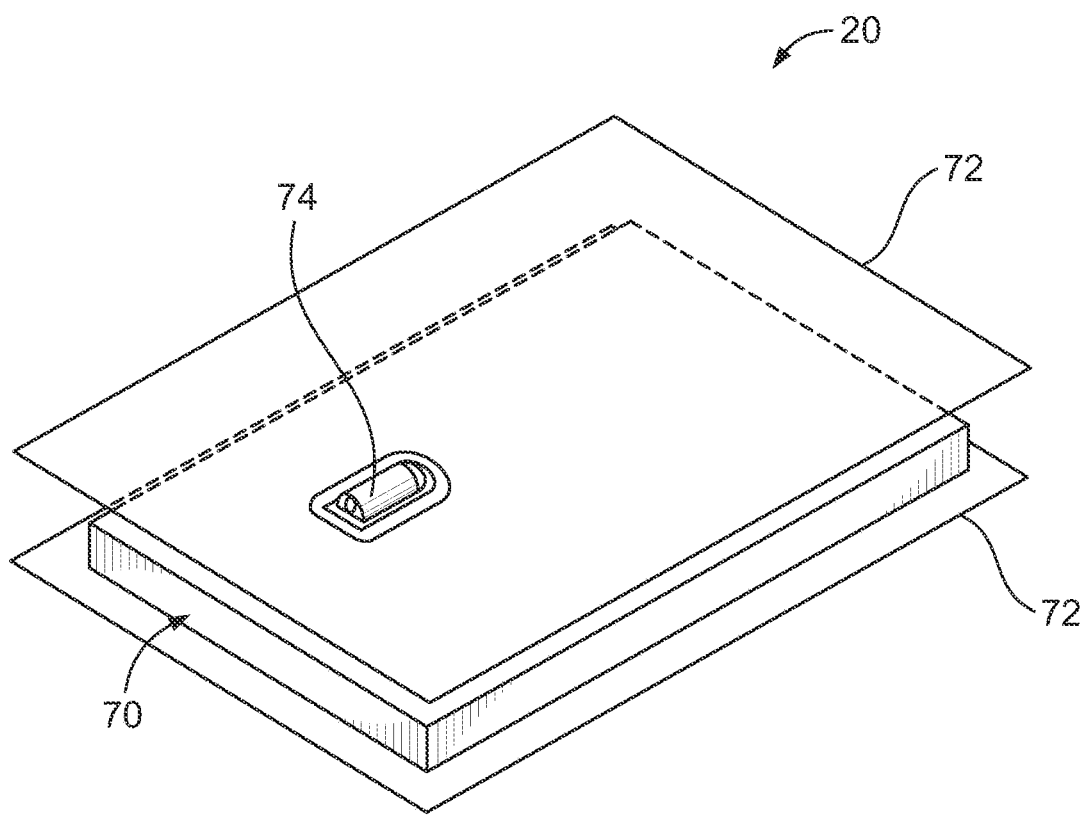
FIG. 3 is an exploded perspective view of the leukoreduction filter of FIG. 2, according to an exemplary embodiment.

For reducing the number of leukocytes that may be present in the separated red blood cells, the disposable fluid flow circuit 10 may include a leukocyte reduction filter or leukoreduction filter 20, which may be of any suitable well known construction for removing leukocytes from concentrated red blood cells without unduly causing homolysis of red blood cells or reducing the number of red blood cells in the collected product. Examples of suitable leukocyte reduction filters may be found in U.S. patent application Ser. Nos. 14/222,961; 14/223,511; and Ser. No. 14/223,831, all of which are incorporated herein by reference in their entireties. FIGS. 2 and 3 illustrate an exemplary leukoreduction filter 20, which may include a filter medium 70 positioned between two flexible walls 72 (FIG. 3), which may be sealed together to prevent leakage of fluid passing through the filter

20. In one embodiment (FIG. 1), the filter 20 may be associated with the outlet flow path 68, with the separated red/white blood cells flowing out of the membrane separator 12, through the primary fluid constituent flow path 48 of the outlet flow path 68, and into the leukoreduction filter 20. The red blood cells may pass from an inlet 74 of the leukoreduction filter 20 to an outlet (not illustrated), passing through the filter medium 70, which may retain leukocytes but not a majority of the red blood cells. After exiting the filter 20, concentrated red blood cells may flow through a continuation 76 of the outlet flow path 68 into a storage container 22, which may be of any suitable material compatible with red blood cell storage.

After a separation procedure is complete, the leukofilter 20 may contain functional white blood cells, such as T-cells, B-cells, and granulocytes (e.g., neutrophils) suitable for cellular, cancer, etc. therapies. The white blood cells may be backflushed and harvested by flowing a suitable solution of phosphate buffered saline (PBS) mixture. The backflush solution is preferably a solution conducive to cell preservation. Granulocytes, such as neutrophils, have been known to survive in a leukofilter up to 24 hours after collection of whole blood, so backflushing may preferably take place within 24 hours of whole blood collection according to an exemplary embodiment. Lymphocytes, such as T-cells and B-cells, have been known to survive in a leukofilter up to 14 days after collection of whole blood, so backflushing may preferably take place within 14 days of whole blood collection according to an exemplary embodiment.

Figure 4:
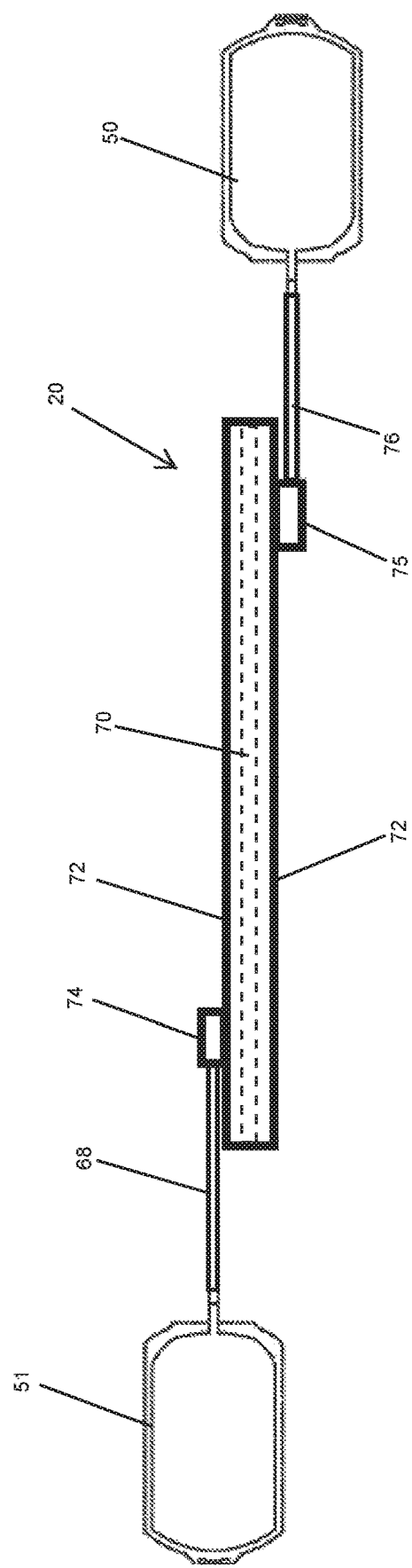
FIG. 4 is a lateral view of a leukoreduction filter including containers attached to the filter's inlet and outlet, according to an exemplary embodiment.

Turning to FIG. 4, the leukofilter 20 may be disconnected from the fluid flow circuit 10 (FIG. 1) by sterilely severing a portion of outlet flow path 68 and a portion of the continuation 76 of the outlet flow path 68. FIG. 4 depicts a lateral view of the leukofilter 20 having a portion of flow path 68 attached to the filter inlet 74 and a portion of flow path 76 attached to the filter outlet 75. A container 50 holding a backflush solution may be sterilely connected to the portion of flow path 76 attached to the filter outlet 75. A container 51 may be sterilely connected to the portion of flow path 68 attached to the filter inlet 74. Container 51 may be empty or may contain a cell preservative/additive solution or other solution suitable for long term or short term storage of white blood cells. Containers 50 and 51 may be any suitable container, such as the TRANSFER-PACK® product marketed by Fenwal, Inc. of Lake Zurich, Ill.

In one embodiment, the backflush solution held in container 50 may comprise a sugar and PBS (with or without ethylenediaminetetraacetic acid (EDTA)). In one embodiment, the sugar may be L-rhamnose. The addition of a sugar such as L-rhamnose to PBS has been shown in studies performed in the development of the present embodiments to increase the concentration of white blood cells removed from the leukofilter. In an embodiment in which the sugar added is L-rhamnose, the backflush solution may be formulated by preparing a phosphate buffered saline containing a concentration of 25-100 mM L-rhamnose. In one embodiment, calcium and/or magnesium may be absent from the backflush solution to minimize aggregation of platelets that may have been captured by the leukofilter. In another embodiment, the backflush solution may be formulated by preparing a phosphate buffered saline without calcium/magnesium, containing a concentration of 45-60 mM L-rhamnose. In yet another embodiment, the backflush solution may be formulated by preparing a phosphate buffered saline without calcium/magnesium, containing a concentration of approximately 50 mM L-rhamnose.

Turning to FIG. 4, a suitable volume of the L-rhamnose/PBS mixture described above may be flowed from container 50 to leukofilter outlet 75 via flow path 76. The L-rhamnose/PBS mixture may be flowed by gravity, manual or non-manual pressure exerted upon container 50, active pumping, and/or any suitable method. In one embodiment, a suitable volume of the L-rhamnose/PBS solution may be approximately 125% of the volume capacity of the leukofilter 20. The volume of the leukofilter may be described as the volume of fluid that may be held within the leukofilter at a time. For example, in an embodiment in which the volume of leukofilter 20 is 40 mL, a suitable volume of the L-rhamnose/PBS solution to be flowed may be approximately 50 mL or more. In an embodiment in which the volume of leukofilter 20 is 25 mL, a suitable volume of the L-rhamnose/PBS solution to be flowed may be approximately 31 mL or more. In an embodiment in which the volume of leukofilter 20 is 100 mL, a suitable volume of the L-rhamnose/PBS solution to be flowed may be approximately 125 mL or more.

From outlet 75, the L-rhamnose/PBS solution may be allowed to permeate the leukofilter 20 and wash the white blood cells captured by the filter 20 towards the filter inlet 74. Flow from outlet 75 to inlet 74 may be effected and/or controlled by gravity, manual or non-manual pressure exerted upon container 50, active pumping, and/or any suitable method. The L-rhamnose/PBS elute containing recaptured white blood cells may be collected into container 51 via flow path 68.

Once the first volume of L-rhamnose/PBS elute containing recaptured white cells has been collected into container 51 second volume of the L-rhamnose/PBS mixture may be flowed from container 50 to leukofilter outlet 75 via flow path 76. The second volume of the L-rhamnose/PBS mixture may be the same or different from the first volume. The second volume may preferably also be approximately 125% of the volume capacity of the leukofilter. The second volume of the L-rhamnose/PBS mixture may be flowed by gravity, manual or non-manual pressure exerted upon container 50, active pumping, and/or any suitable method.

From outlet 75, the second volume of the L-rhamnose/PBS solution may be allowed to again permeate the leukofilter 20 and wash any remaining white blood cells within the filter 20 towards the filter inlet 74. Flow from outlet 75 to inlet 74 may be effected and/or controlled by gravity, manual or non-manual pressure exerted upon container 50, active pumping, and/or any suitable method. The second volume of the L-rhamnose/PBS elute containing any remaining white blood cells may be collected into container 51 via flow path 68. Depending on the desired number of white blood cells or efficiency of white blood cells to be captured from leukofilter 20, additional volumes of L-rhamnose/PBS solution may be passed through the leukofilter 20 in a similar manner.

In one embodiment, the resulting combined product of the L-rhamnose/PBS elute containing white blood cells collected in container 51 may comprise a white blood cell concentration within the range of $4.5 \times 10^3$ to $7.0 \times 10^3$ cells per uL. In another embodiment, the resulting combined product of the L-rhamnose/PBS elute containing white blood cells collected in container 51 may comprise a white blood cell concentration within the range of $5.0 \times 10^3$ to $6.5 \times 10^3$ cells per uL. In yet another embodiment, the resulting combined product of the L-rhamnose/PBS elute containing white blood cells collected in container 51 may comprise a white blood cell concentration of approximately $6.0 \times 10^3$ cells per uL.

Figure 5:
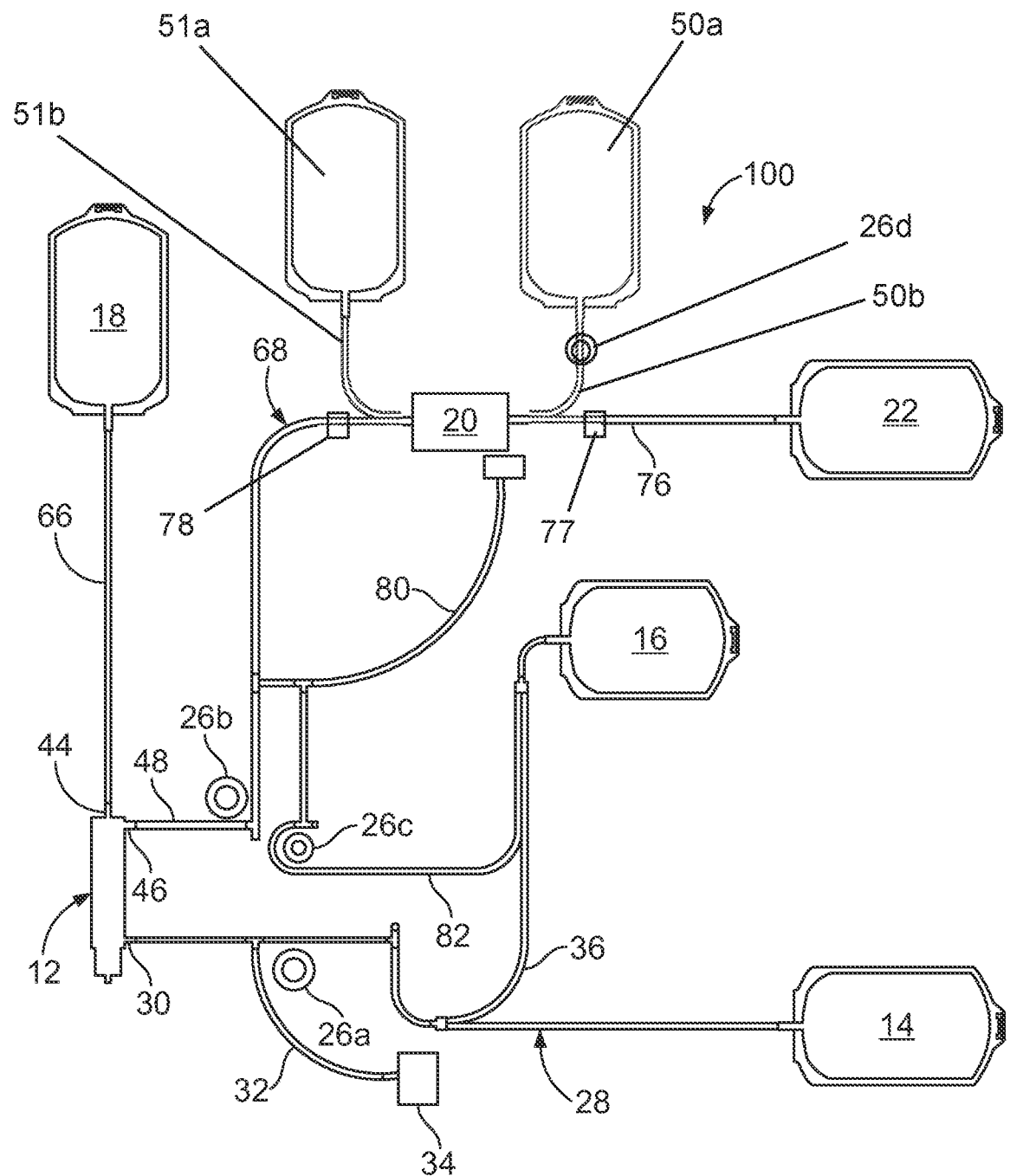
FIG. 5 is a front elevational view of a disposable fluid flow circuit configured for recovering white blood cells from a leukoreduction filter, according to an exemplary embodiment.

FIG. 5 illustrates a disposable fluid flow circuit 100 similar to the disposable circuit 10 of FIG. 1. FIG. 5 shows the flow circuit additionally having a container 50*a* holding a backflush solution connected to the portion of the flow path attached to the filter outlet (not illustrated) of leukofilter 20 (e.g., such as shown in FIG. 4). Container 50*a* holding the backflush solution may be integrally connected to the fluid circuit 100 at the time of manufacture or sterilely connected at a later time according to any suitable method. FIG. 5 shows the flow circuit also having a container 51*a* connected to the portion of flow path 68 attached to the filter inlet (not illustrated) for receiving backflushed white blood cells (e.g., such as shown in FIG. 4). Container 51*a* may be empty or may contain a cell preservative/additive solution or other solution suitable for long term or short term storage of white blood cells. Container 51*a* may be integrally connected to the fluid circuit 100 at the time of manufacture or sterilely connected at a later time according to any suitable method. Containers 50*a* and 51*a* may be any suitable container, such as the previously mentioned TRANSFER-PACK® product.

A programmable controller (e.g., microprocessing unit) driven by software that is part of the durable hardware component may activate pump 26*a* to pump the white blood cell-containing fluid in container 14 through inlet flow path 28 into inlet 30 of the separator 12. A secondary fluid constituent, such as plasma, separated by the separator 12 may flow from outlet port 44, through the secondary fluid constituent flow path 66, and into storage container 18. Similarly, from the separator 12, a primary fluid constituent, such as red blood cells and/or white blood cells may flow through outlet port 46 and through primary fluid constituent flow path 48, which may form part of an outlet flow path 68. The programmable controller may be configured to pump the separated red/white blood cells through the outlet flow path 68 by activating red/white blood cell or outlet pump 26*b* of the blood separation system. The outlet pump 26*b* may be configured and operate substantially the same way as the inlet pump 26*a* or it may be differently configured (e.g., as a flexible diaphragm pump). In an embodiment in which the separator 12 is a membrane separator, the secondary fluid constituent flow path 66 may lack an associated pump, as the volumetric flow rate therethrough may be effected by the difference between the volumetric flow rate of the inlet pump 26*a* and the volumetric flow rate of the outlet pump 26*b*. During pumping of the separated red/white blood cells through flow path 68, flow path 51*b* leading to container 51*a* may be clamped, to ensure that fluid flow is directed into leukofilter 20.

Within the leukofilter 20, white blood cells and other retentate may be captured by the filter material, while a majority of the red blood cells and other leukofilter filtrate may be pumped under the direction of the programmable controller into container 22 via flow path 76. A pump 26*d* may be in place at flow path 50*b* leading to container 50*a* holding the backflush solution. Pump 26*d* may be inactive and also function as a clamp blocking fluid flow into container 50*a*, ensuring that the red blood cells and other leukofilter filtrate are directed into container 22.

When separation of primary and secondary fluid constituents has taken place and all leukofilter filtrate matter has been received by container 22, the programmable controller may inactivate pump 26*b* and activate pump 26*d* to pump a suitable first volume of the L-rhamnose/PBS mixture within container 50*a* from container 50*a* to the leukofilter 20 via flow path 50*b*. At this time, a portion of the flow path 76 disposed between flow path 50*b* and container 22 may be clamped shut by a clamp 77 to ensure that the backflush solution is directed into the leukofilter 20. In one embodiment, a suitable first volume of the L-rhamnose/PBS solution may be approximately 125% of the volume capacity of the leukofilter 20.

Within the leukofilter 20, the L-rhamnose/PBS solution may be allowed to permeate the leukofilter 20 and wash the white blood cells captured by the filter 20 towards the filter inlet (not illustrated). Flow from the leukofilter 20 to the filter inlet may be effected by the active pumping of pump 26*d*. At this time, a portion of the flow path 68 disposed between flow path 51*b* and pump 26*b* may be clamped shut by a clamp 78 to ensure that the L-rhamnose/PBS elute containing recaptured white blood cells is directed into flow path 51*b* and into container 51*a*.

Once the first volume of L-rhamnose/PBS elute containing recaptured white cells has been collected into container 51*a*, a second volume of the L-rhamnose/PBS mixture may be pumped from container 50*a* to the leukofilter 20 via flow path 50*b* to permeate the leukofilter 20 and wash the white blood cells captured by the filter 20. The second volume of the L-rhamnose/PBS mixture may be the same or different from the first volume. The second volume may preferably also be approximately 125% of the volume capacity of the leukofilter. The second volume of the L-rhamnose/PBS elute containing any remaining white blood cells may be collected into container 51*a* via flow path 51*b*. Depending on the desired number of white blood cells or efficiency of white blood cells to be captured from leukofilter 20, additional volumes of L-rhamnose/PBS solution may be passed through the leukofilter 20 in a similar manner.

In another embodiment, a single volume of L-rhamnose/PBS mixture may be pumped continuously by pump 26*d* from container 50*a* through flow path 50*b* through the leukofilter 20 through flow path 51*b* and into container 51*a* rather than as a batch process. For example, in an embodiment in which the volume of leukofilter 20 is 40 mL, approximately 100 mL or more of the L-rhamnose/PBS solution may be continuously pumped through leukofilter 20 to continuously backflush white blood cells into container 51*a*.

In one embodiment, the resulting combined product of the L-rhamnose/PBS elute containing white blood cells collected in container 51*a* may comprise a white blood cell concentration within the range of $4.5 \times 10^3$ to $7.0 \times 10^3$ cells per uL. In another embodiment, the resulting combined product of the L-rhamnose/PBS elute containing white blood cells collected in container 51*a* may comprise a white blood cell concentration within the range of $5.0 \times 10^3$ to $6.5 \times 10^3$ cells per uL. In yet another embodiment, the resulting combined product of the L-rhamnose/PBS elute containing white blood cells collected in container 51*a* may comprise a white blood cell concentration of approximately $6.0 \times 10^3$ cells per uL.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A method of recovering white blood cells from a leukoreduction filter, the method comprising:
   providing a solution comprising a sugar; wherein the sugar is L-rhamnose;
   flowing a volume of the solution through a leukoreduction filter containing captured white blood cells; and collecting elute from the leukoreduction filter, wherein the elute comprises the solution and recovered white blood cells.

2. The method of claim 1, wherein the solution has a L-rhamnose concentration in the range of 25 to 100 mM.

3. The method of claim 1, wherein the volume of the solution flowed through the leukoreduction filter is approximately 125% of a volume capacity of the leukoreduction filter.

4. The method of claim 1, wherein the volume of the solution is flowed through the leukoreduction filter by at least one of gravity flow, active pumping, and manual pressure.

5. The method of claim 1, further comprising flowing a second volume of the solution through the leukoreduction filter containing captured white blood cells and collecting a second elute from the leukoreduction filter, wherein the second elute comprises the solution and white blood cells recovered by the second volume of the solution.

6. The method of claim 1, wherein the elute collected from the leukoreduction filter comprises a white blood cell concentration within the range of $4.5 \times 10^3$ to $7.0 \times 10^3$ cells per uL.

7. A method for automated recovery of white blood cells from a leukoreduction filter, the method comprising:
providing a durable separation hardware controlled by a programmable controller driven by software, said hardware configured to associate with a disposable sterile circuit comprising a separator and a leukoreduction filter, wherein the hardware and disposable sterile circuit are configured by the programmable controller to:
separate a white blood cell-containing fluid into a primary fluid constituent and a secondary fluid constituent;
collect the secondary fluid constituent in a first container;
direct in a first flow direction the primary fluid constituent through a leukoreduction filter configured to capture white blood cells and other retentate while not capturing filtrate;
collect the filtrate flowing out of the leukoreduction filter in a second container;
direct in a second flow direction a volume of solution comprising a sugar through the leukoreduction filter; wherein the sugar is L-rhamnose; and
collect in a third container a first volume of elute flowing out of the leukoreduction filter, wherein the first volume of elute comprises the solution and recovered white blood cells.

8. The method of claim 1, wherein the solution has a L-rhamnose concentration in the range of 25 to 100 mM.

9. The method of claim 7, wherein the solution further comprises phosphate buffered saline and the white blood cell-containing fluid is whole blood.

10. The method of claim 7, wherein the separator is a centrifugal separator.

11. The method of claim 7, wherein the separator is a spinning membrane separator.

12. The method of claim 7, wherein the volume of the solution directed through the leukoreduction filter is approximately 125% of a volume capacity of the leukoreduction filter.

13. The method of claim 7, further comprising directing in the second flow direction a second volume of the solution through the leukoreduction filter and collecting a second volume of elute from the leukoreduction filter, wherein the second volume of elute comprises the solution and white blood cells recovered by the second volume of the solution.

14. The method of claim 13, wherein the first and second volumes of elute collected from the leukoreduction filter together comprise a white blood cell concentration within the range of $4.5 \times 10^3$ to $7.0 \times 10^3$ cells per uL.

* * * * *